United States Patent [19]

Nodari et al.

[11] Patent Number: 5,730,908
[45] Date of Patent: Mar. 24, 1998

[54] PHOTOCHROMATIC AND THERMOCHROMATIC COMPOUNDS AND THEIR APPLICATION IN POLYMERIC MATERIALS

[75] Inventors: Nereo Nodari, Pantigliate; Pietro Allegrini, San Donato Milanese; Luciana Crisci, Graffignana, all of Italy

[73] Assignee: Enichem Synthesis S.P.A., Palermo, Italy

[21] Appl. No.: 217,075

[22] Filed: Mar. 24, 1994

Related U.S. Application Data

[63] Continuation of Ser. No. 918,833, Sep. 21, 1992, abandoned.

[30] Foreign Application Priority Data

Jul. 24, 1991 [IT] Italy ................... MI91A2038

[51] Int. Cl.$^6$ .............. G02B 5/23; G02F 1/00; C07D 265/00
[52] U.S. Cl. .............. 252/586; 544/71; 252/583
[58] Field of Search .................. 252/582, 586, 252/583; 544/71

[56] References Cited

U.S. PATENT DOCUMENTS

| | | | |
|---|---|---|---|
| 3,562,172 | 2/1971 | Ono et al. | 252/586 |
| 3,578,602 | 5/1971 | Ono et al. | 252/586 |
| 4,215,010 | 7/1980 | Hovey et al. | 252/586 |
| 4,342,668 | 8/1982 | Hovey et al. | 252/586 |
| 5,166,345 | 11/1992 | Akashi et al. | 544/71 |

FOREIGN PATENT DOCUMENTS

| | | |
|---|---|---|
| 0146135 | 12/1984 | European Pat. Off. . |
| 146135 | 12/1984 | European Pat. Off. . |
| 0134633 | 3/1985 | European Pat. Off. . |
| 0141407 | 5/1985 | European Pat. Off. . |
| 0230024 | 7/1987 | European Pat. Off. . |
| 0245020 | 11/1987 | European Pat. Off. . |
| 245020 | 11/1987 | European Pat. Off. . |
| 0277639 | 8/1988 | European Pat. Off. . |
| 0350009 | 1/1990 | European Pat. Off. . |
| 0449669 | 10/1991 | European Pat. Off. . |
| WO 8502619 | 6/1985 | WIPO . |

OTHER PUBLICATIONS

World Patents Index Latest, Section Ch: Week 9130, Derwent Publications Ltd. London, GB; Class A, AN–91217705 & JP–A–3 137 634 (Dainippon Ink Schem Ink KK) 12, Jun. 1991; "abstract".

World Patents Index Latest, Section Ch, Week 9125, Derwent Publications Ltd., London, GB; Class E, AN 91180613 & JP–A–3 107 839 (Hitachi KK) 8 May 1991, "abstract".

La Chemica E L'Industria, vol. 69, No. 9, Sep. 87 Specific Solvation and Reactivity of Anions in Catalysis Conditions for Transferral of Phase and in Solvents at Low Polarities, (1987).

*Primary Examiner*—Philip Tucker
*Attorney, Agent, or Firm*—George P. Hoare; Rogers & Wells

[57] ABSTRACT

A description follows of photochromatic and thermochromatic compounds, belonging to the group of spiro-indoline-oxazines, and their application in polymeric materials.

10 Claims, No Drawings

PHOTOCHROMATIC AND THERMOCHROMATIC COMPOUNDS AND THEIR APPLICATION IN POLYMERIC MATERIALS

This is a continuation of Ser. No. 07/918,833 filed Sep. 21, 1992, now abandoned.

The present invention relates to photochromatic and thermochromatic compounds, belonging to the group of spiro-indoline-oxazines, and their application in polymeric materials.

Photochromatic compounds are substances which have the characteristic of reversibly changing colour and/or degree of light transmission when exposed to certain types of electromagnetic radiations and solar light, returning to their original state of colour and transmission when the initial light source is removed.

There are many known substances having photochromatic characteristics, belonging to different groups of both inorganic and organic compounds, as can be seen, for example, in the texts "Photochromism"; by G. H. Brown (Ed.), Vol. III of the Weissberger series "Techniques of Organic Chemistry", Wiley Interscience, New York (1971) and in "Photochromism. Molecules and Systems", by H. D ürr and H. Bouas-Laurent (Ed.), Vol. 40 of the series "Studies in Organic Chemistry", Elsevier (1990).

Among the organic photochromatic compounds, particularly well-known are those of the group of spiro-indoline-oxazines which are capable of plying photochromatic characteristics to polymerized organic materials, used as photochromatic articles, as described for example in U.S. Pat. Nos. 3,562,172, 3,578,602, 4,215,010, 4,342,668, EP 146,135, WO 85/02619, EP 245,020, EP 134,633, EP 141, 407 and in Italian Patent Applications IT 22529 A/87, IT 22660 A/89 and IT 19389 A/90 in, the name of the Applicant.

Known photochromatic compounds of the spiro-indoline-oxazine group, compared to other known organic photochromatic compounds (for example those belonging to the group of spiro-pyranes), have the advantage of having a much higher fatigue resistance when submitted to repeated coloration and decoloration cycles and a much greater aging resistance on exposure to solar light or in artificial aging tests.

This behaviour is extremely advantageous for the above-mentioned uses.

The photochromatic compounds belonging to the group of spiro-indoline-oxazines of the known art cannot be used however in some polymeric materials such as high-density polyethylene, low-density polyethylene, ethylene-vinylacetate copolymer, polyether amides such as, for example PEBAX (Atochem).

In these matrices, in fact, the photochromatic compound tends to appear on the surface of the product causing a phenomenon known as "blooming".

This draw-back prevents the above compounds from being applied in various fields such as agricultural covering sheets, bags, packaging and generally in areas where the above polymers are used.

We have now synthesized, and this forms the first aspect of the present invention, photochromatic and thermochromatic compounds, belonging to the spiro-indoline-oxazine group, having substituents composed of long alkyl chains, which overcome the above disadvantages of the known art.

A second aspect of the present invention relates to the photochromatic polymeric compositions obtained by superficially applying or incorporating the above compounds into suitable polymers.

The compounds of the present invention can be defined with the following general formula (I):

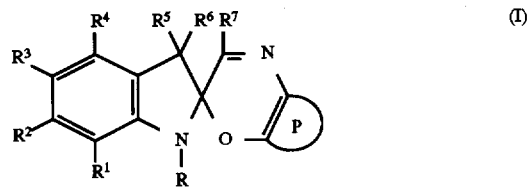

wherein:

1) R represents a hydrogen atom; a $C_1$–$C_5$ alkyl group linear or branched; a $C_1$–$C_5$ alkyl group substituted with from 1 to 5 halogen atoms selected from fluorine, chlorine, bromine and iodine, hydroxy groups, $C_1$–$C_5$ alkyoxy groups, $C_1$–$C_5$ alkyl carboxy groups, cyano groups; a $C_2$–$C_5$ alkenyl group; a phenyl group; a benzyl group;

2) $R^1$ to $R^4$, the same or different, each independently represent a hydrogen atom; a linear or branched $C_1$–$C_5$ alkyl group; a $C_1$–$C_5$ alkyl group substituted with from 1 to 5 halogen atoms selected from fluorine, chlorine, bromine and iodine, hydroxy groups, $C_1$–$C_5$ alkoxy groups, $C_1$–$C_5$ alkyl carboxy groups, cyano groups; a $C_{2-5}$ alkenyl group; a benzyl group; a halogen atom selected from fluorine, chlorine, bromine and iodine; a hydroxy group; a $C_1$–$C_5$ alkoxy group; an amino group; a mono-alkyl ($C_1$–$C_5$) amino group; a di-alkyl ($C_1$–$C_5$) amino group; a cyclo-alkyl ($C_3$–$C_{10}$) amino group; a piperidino, piperazino or morpholino group; a carboxyl group; a $C_1$–$C_5$ alkyl carboxy group; a $C_{2-5}$ alkenyl carboxy group; an amidic carboxy group; a substituted N-alkyl ($C_1$–$C_5$) amidic carboxy group; a substituted N,N-dialkyl ($C_1$–$C_5$) amidic carboxy group; a cyano group; a nitro group; a sulphonic group; a sulphonic alkyl ($C_1$–$C_5$) group; a trifluoromethan-sulphonic group; a sulphonic aryl group selected from sulphonic benzene groups, sulphonic p-toluene groups, sulphonic p-chlorotoluene groups; an aryl group selected from phenyl, biphenyl, naphthyl groups; an acylic group of the ketone alkyl, ketone aryl or ketone benzyl type;

3) two consecutive substituents from $R^1$ to $R^4$ can represent the fusion sites with other aromatic, heterocyclic or quinonic rings;

4) $R^5$ and $R^6$, the same or different, each independently represent a linear or branched $C_1$–$C_5$ alkyl group; a phenyl group; or $R^5$ and $R^6$, together with the carbon atom to which they are linked, jointly represent a $C_4$–$C_7$ cycloalkyl group;

5) $R^7$ represents a hydrogen atom; a linear or branched $C_1$–$C_5$ alkyl group; a phenyl group; a halogen atom selected from fluorine, chlorine and bromine; a $C_1$–$C_5$ alkoxy group, a phenoxy group;

6) P represents a monocyclic or polycyclic arenic nucleus, of the benzene, naphthalene, quinoline, isoquinoline or cumarin type which can be respectively represented by formulae (II), (III), (IV), (V) and (VI):

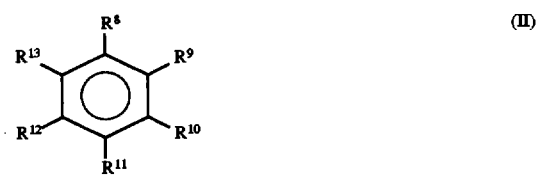

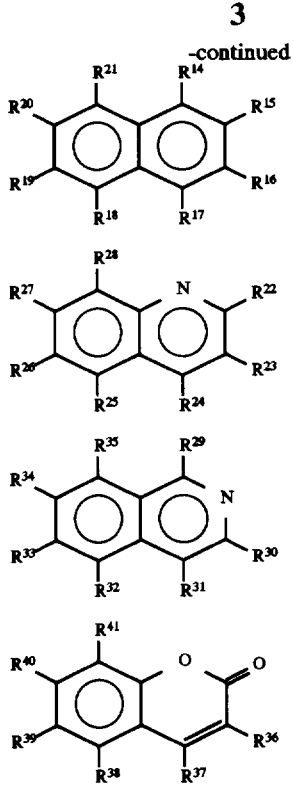

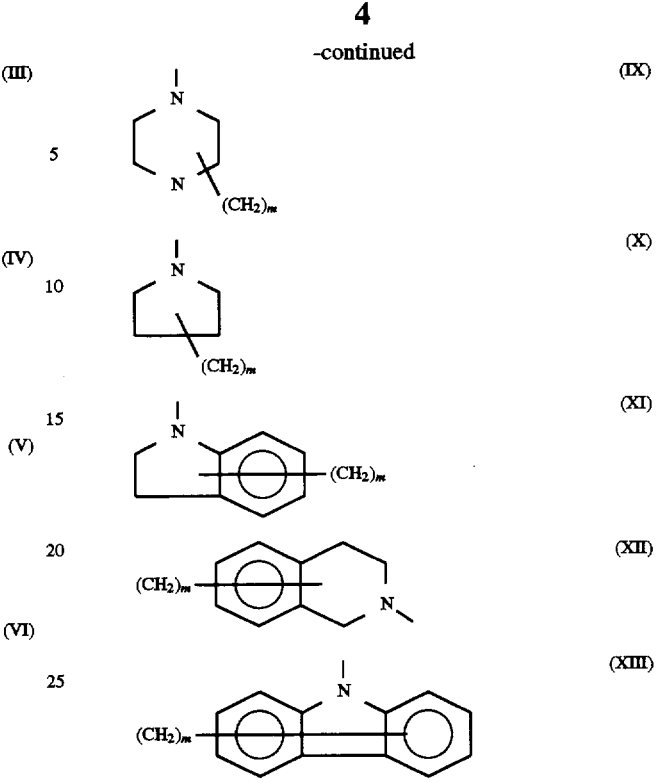

wherein m is an integer from 0 to 10.

wherein:

6a) at least two contiguous substituents from $R^8$ to $R^{13}$, $R^{14}$ to $R^{21}$, $R^{22}$ to $R^{28}$, $R^{30}$ to $R^{35}$, $R^{36}$ to $R^{41}$ represent the fusion with the oxazinic ring;

6b) the substituents from $R^8$ to $R^{41}$ have the meaning defined in point 2 );

7 ) at least one of the substituents selected from R–$R^{41}$ represents an $R^{42}$ group, a —COOR$^{42}$, —CONHR$^{42}$, —CONR$^{42}$R$^{43}$, —COR$^{42}$, OH—CH—R$^{42}$, OH—C—R$^{42}$R$^{43}$, —OR$^{42}$, —NHR$^{42}$, NR$^{42}$R$^{43}$, —SR$^{42}$, —O—(CH$_2$)$_n$—COOR$^{42}$, —O—(CH$_2$)$_n$—CONHR$^{42}$, —O—(CH$_2$)—CONR$^{42}$R$^{43}$ group wherein n varies from 0 to 10 and $R^{42}$ and $R^{43}$ can independently be a linear or branched C$_6$–C$_{30}$ alkyl group; a C$_6$–C$_{30}$ alkyl group substituted with 1–30 halogen atoms selected from fluorine, chlorine, bromine or iodine; a C$_6$–C$_{30}$ alkenyl group.

Substituents $R^1$–$R^{41}$ may otherwise be groups represented by formulae (VII)–(XIII):

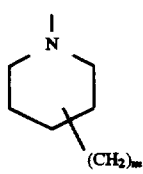

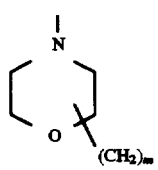

In the preferred method, in formula (I):

R represents a methyl, ethyl, benzyl, 2-allyl, 2-hydroxyethyl, 2-methoxyethyl or 2-carboxymethylethyl group;

$R^1$ to $R^4$, the same or different, each independently represent the hydrogen atom, a fluorine, chlorine or bromine atom, a methyl, isopropyl, trifluoromethyl, hydroxymethyl, benzyl, hydroxy, methoxy, amino, piperidino, morpholino, carboxyl, carboxymethyl, N,N-dimethylcarboxyamide, cyano, nitro or phenyl group;

$R^5$ and $R^6$, the same or different, each independently represent a methyl or phenyl group or, together with the carbon atom to which they are linked, jointly represent a cyclohexyl group;

$R^7$ represents the hydrogen atom, chlorine atom or phenyl, methyl or methoxy group;

P is one of the groups with a formula from (II) to (VI) wherein:

two contiguous substituents from $R^8$ to $R^{13}$, $R^{14}$ to $R^{21}$, $R^{22}$ to $R^{28}$, $R^{30}$ to $R^{35}$, $R^{36}$ to $R^{41}$ independently represent the fusion sites with the oxazinic ring in the general formula (I) and the others, each independently, represent the hydrogen atom, a fluorine, chlorine or bromine atom, a methyl, isopropyl, trifluoromethyl, hydroxymethyl, benzyl, hydroxy, methoxy, amino, piperidino, morpholino, carboxyl, carboxymethyl, N,N-dimethylcarboxyamide, cyano, nitro, phenyl, acetyl or benzoyl group;

two contiguous sustituents from $R^8$ to $R^{13}$, $R^{14}$ to $R^{21}$, $R^{22}$ to $R^{28}$, $R^{30}$ to $R^{35}$, $R^{36}$ to $R^{41}$ represent the fusion sites with a benzene or quinone ring;

at least one of the substituents from R–$R^{41}$ represents what has already been described in point 7).

Specific examples of preferred photochromatic compounds according to the present invention, are:

-1,3-dihydro-6'-N[2(octadecanoyloxy)ethyl] piperazino-1,3,3-trimethyl spiro [2H indole-2,3'-[3H]-naphth-(2,1b)-(1,4) oxazine] (Ia);

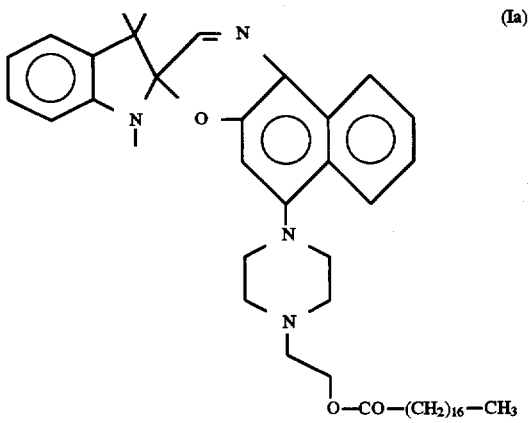

-1,3-dihydro-9'-dodecyloxy-1,3,3-trimethyl spiro [2H indole-2,3'-[3H]-naphth-(2,1b)-(1,4) oxazine] (Ib);

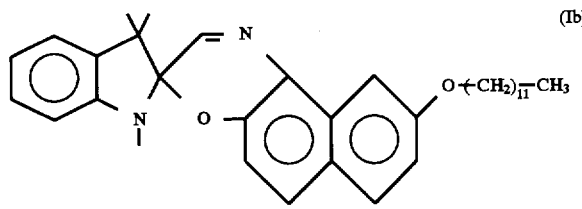

- 1,3-dihydro-9'-(octadecyloxyacetate)-1,3,3-trimethyl spiro [2H indole-2,3'-[3H]-naphth-(2,1b)-(1,4) oxazine](Ic);

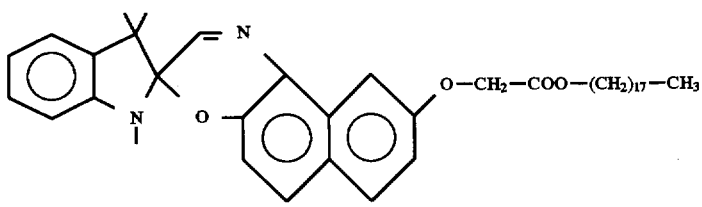

Compounds (I), of the present invention can be prepared by the reaction of a nitroso derivative of the compounds having formula (II), (III), (IV), (V), (VI), wherein two continuous substituents from $R^8$ to $R^{13}$, from $R^{14}$ to $R^{21}$, from $R^{22}$ to $R^{28}$, from $R^{30}$ to $R^{35}$, and from $R^{36}$ to $R^{41}$ represent one a —N═O group and the other a —$OR^{44}$ group, wherein $R^{44}$ is a hydrogen atom; a metallic cation selected from sodium, potassium, lithium and copper cations; an ammonium or dialkyl ($C_1$–$C_5$) ammonium cation; a carbonylalkyl ($C_1$–$C_5$) group; an alkyl ($C_1$–$C_5$) sulphonyl group or an arylsulphonyl group; with a compound having formula (XIV):

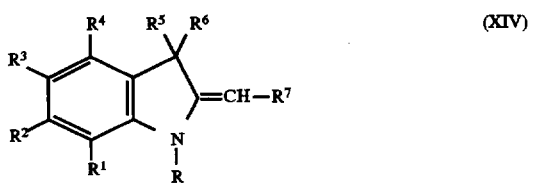

wherein the substituents from R to $R^7$ have the above-defined meaning.

The nitroso derivatives of compounds (II), (III), (IV), (V), and (VI) can be prepared using the known methods described in Organic Synthesis Collective, vol. 3, page 411 or in U.S. Pat. No. 3,285,972.

Compounds (XIV) can also be prepared with the known methods, as described in Journal American Chemical Society (1941), 63, page 2024 or in Bull. Soc. Chim. Frac. (1968), page 2066.

The reaction is generally carried out by adding compound (XIV) to a solution or suspension of the nitroso derivative of one of compounds (II), (III), (IV), (V) or (VI), in an inert organic solvent, possibly in the presence of a secondary or tertiary amine, operating at a temperature ranging from 0° to 150° C. and preferably from 0° to 80° C., for periods of 1 minute to 24 hours.

The inert solvents which can be used for the reaction can be selected from aliphatic or aromatic hydrocarbons (such as pentane, hexane, heptane, benzene, toluene and xylene); chlorinated aliphatic or aromatic hydrocarbons (such as dichloromethane, 1,2-dichloroethane and chlorobenzene); aliphatic or aromatic ethers (such as diethyl ether, tetrahydrofuran and diphenylether); alcohols (such as methanol, ethanol, isopropanol and n-butanol); esters (such as ethyl acetate); amides (such as dimethylformamide); nitriles (such as acetonitrile); carbonates (such as dimethylcarbonate); and water.

In the reaction, the nitroso derivatives of compounds (II), (III), (IV), (V) or (VI) can be used in quantities ranging from 0.1 to 10 moles for each mole of compound (XIV), but preferably with equimolecular quantities.

When the reaction is carried out in the presence of a tertiary amine, this can be used in quantities of 0.1 to 2 moles for each mole of nitroso derivative, but preferably equimolecular quantities are used.

Examples of tertiary amines suitable for the purpose are: triethylamine, pyridine, 4-N,N-dimethylaminopyridine, N-methylpiperidine and N-methylmorpholine.

When the reaction is carried out in the presence of a secondary amine, this can be used in quantities ranging from 1 to 10 moles for each mole of nitroso derivative, but preferably from 2 to 5 moles.

Examples of secondary amines suitable for the purpose are: N-2-hydroxyethylpiperazine, N-2-aminoethylpiperazine and those described in EP Patent 245.020 and in IT Patent Application 22528 A/87 in the name of the same Applicant.

Alternatively, compounds (I) of the present invention can be prepared by the condensation of compounds having formula A, with a structure defined by the general formula (I), wherein the substituents and the nucleus P represent what has been previously described except for point 7) and at least one of the substituents from R–$R^{41}$ represents a hydroxy group, an amino group, a monoalkylamino group, an SH group directly linked to the spiro-oxazinic nucleus, by means of groups having formula —O—$(CH_2)_n$—, wherein n is an integer from 0 to 10, or by means of groups having formula (VII)–(XIII); with compounds having formula $R^{45}$—CO—$R^{46}$, wherein $R^{45}$ represents a linear or branched $C_6$–$C_{30}$ alkyl group, a $C_6$–$C_{30}$ alkyl group substituted with 1–30 halogen atoms selected from fluorine, chlorine, bromine or iodine or a linear or branched $C_6$–$C_{30}$ alkenyl group and $R^{46}$ represents a linear or branched $C_1$–$C_6$ alkoxy group, a hydroxy group, a halogen atom selected from chlorine, bromine or an imidazolic group.

The condensation is carried out under the conditions described in literature for the preparation of derivatives of carboxylic acids.

Compounds (I) of the present invention can also be prepared by the reaction between compounds having formula A, wherein the substituents and the nucleus P represent what is described above, and compounds having formula $R^{45}$—X, wherein $R^{45}$ represents what has already been described and X is a halogen atom selected from chlorine, bromine or iodine, an acetate group, a methanesulphonate group or a p-toluene-sulphonate group.

In this case the reaction is generally carried out by mixing the reagents in a solvent or mixture of inert solvents, possibly in the presence of basic compounds and/or phase transfer catalysts, operating at a temperature ranging from 0° to 200° C., preferably from 10° to 120° C., for periods of 1 minute to 48 hours.

Inert solvents which can be used for The reaction can be selected from aliphatic or aromatic hydrocarbons (such as pentane, hexane, heptane, benzene, toluene and xylene); chlorinated aliphatic or aromatic hydrocarbons (such as dichloromethane, 1,2-dichloroethane and chlorobenzene); aliphatic or aromatic ethers (such as diethyl ether, tetrahydrofuran and diphenylether); alcohols (such as methanol, ethanol, isopropanol and n-butanol); amides (such as dimethylformamide); ketones (such as acetone); nitriles (such as acetonitrile); dimethylsulphoxide; water; mixtures of at least one of the above organic solvents.

Compounds having formula A, intermediate products for the preparation of compounds (I), are prepared according to the procedure described in Patent Application IT 22528 A/87 in the name of the Applicant.

Compounds having formula R45—X can be used in quantities ranging from 1 to 10 moles for each mole of the compound having formula A but preferably from 1 to 5 moles.

When the reaction is carried out in the presence of basic compounds, these can be used in quantities of 0.1 to 10 moles with respect to the compound having formula R45—X but preferably from 1 to 5 moles.

Examples of basic compounds suitable for the purpose are: carbonates and bicarbonates of alkaline or earth-alkaline metals, such as sodium carbonate, potassium carbonate and calcium carbonate; tertiary amines such as triethylamine, pyridine, 4-N,N-dimethylaminopyridine, N-methylpiperidine and N-methylmorpholine; hydroxides of alkaline or earth-alkaline metals, such as sodium hydroxide, potassium hydroxide and calcium hydroxide; and mixtures of said compounds.

When the reaction is carried out under conditions of phase-transfer catalysis, the known methods may be used such as those described in "La Chimica e l'Industria", vol. 69 n.9, pages 94–98 (1987) and in the references cited therein.

A further method for the synthesis of compounds having formula (I) involves a condensation reaction between compounds having formula B, with a structure defined by general formula (I), wherein the substituents and the nucleus P represent what has been previously described except for point 7) and at least one of the substituents from R–R$^{41}$ represents a CO—R$^{47}$ group directly linked to the spiro-oxazinic nucleus, through groups having formula —O—(CH$_2$)$_n$—, wherein n is an integer from 0 to 10, or through groups having formula (VII)–(XIII); R$^{47}$ represents a hydroxy group, a linear or branched C$_1$–C$_6$ alkoxy group, an imidazolic group, a halogen atom selected from chlorine or bromine; and compounds having the formula R$^{48}$—NH$_2$, R$^{48}$–R$^{49}$—NH, R$^{48}$—OH, R$^{48}$—SH wherein R$^{48}$ and R$^{49}$ represent a linear or branched C$_6$–C$_{30}$ alkyl group, a C$_6$–C$_{30}$ alkyl group substituted with 1–30 halogen atoms selected from fluorine, chlorine, bromine or iodine; a linear or branched C$_1$–C$_{30}$ alkenyl group.

The condensation is carried out under the conditions described in literature for the preparation of derivatives of carboxylic acids.

In general, the products (I), synthesized according to one of the methods mentioned, are isolated using the normal techniques, such as for example, evaporation of the solvent under vacuum with subsequent purification of the raw product obtained by crystallization or chromatography.

Solvents suitable for crystallization include pentane, hexane, heptane, toluene, ethyl ether, methanol, ethanol, isopropanol, n-butanol, tetrahydrofuran, acetone, methylethylketone, ethyl acetate, dimethylcarbonate, acetonitrile and the relative mixtures of one or more of these.

Compounds (I) of the present invention are colourless or yellow, orange or red-coloured crystalline products.

Their solutions in common organic solvents, when not exposed to light sources, are colourless or slightly yellow or yellow-orange coloured.

When these solutions are exposed to a source of light (both visible and ultraviolet) they rapidly acquire a dark yellow, yellow-orange, red, blue or green colouring.

The colouring rapidly diminishes when the light source is removed.

The compounds having formula (I) can be applied either superficially or incorporated in the required articles, using the known techniques hereinafter described.

Some polymeric photochromatic products can be obtained with moulding techniques (for example injection or compression moulding) starting from suitable polymers in which the photochromatic compound is homogeneously dispersed in the mass.

Alternatively the photochromatic compound can be dissolved in a suitable solvent, together with the polymeric material (such as polymethyl methacrylate, polyvinyl alcohol, polyvinyl butyral, cellulose or epoxy, polysiloxanic or urethanic resin acetate butyrate) and deposited on a transparent support to form, after evaporation of the solvent, a photochromatic coating.

The photochromatic compound can also be added to a polymerizable monomer, for example methyl methacrylate, so that, after polymerization carried out in the presence of a suitable initiator, such as azobisisobutyronitrile, they are uniformly incorporated in the resin formed.

According to another procedure, the photochromatic compound can be dissolved in a suitable solvent, in the presence of a resin, as described above, and a photochromatic film or plate containing the photochromatic compound uniformly dispersed can be formed from this solution, by evaporating the solvent.

Finally the photochromatic compound can be applied to a transparent substrate (for example polycarbonate, polymethyl methacrylate or polydiethylene glycol bis(allyl carbonate)), by surface impregnation obtained by putting the substrate in contact with a solution or dispersion containing the photochromatic compound, at a suitable temperature.

Compounds (I) of the present invention have the characteristic of being able to be successfully incorporated, in mass or using one of the above techniques, also in polymers such as high density polyethylene, low density polyethylene, ethylene-vinylacetate copolymer or polyether amides whereas the compounds of the known art, in these substrates, tend to appear on the surface of the product making it consequently unusable.

The experimental examples which follow illustrate the present invention but do not limit it in any way.

EXAMPLE 1

Preparation of 1,3-dihydro-6'-N(-2-hydroxyethyl) piperazino-1,3,3-trimethyl spiro [2H indole-2,3'-[3H]-naphth-(2,1b)-(1,4) oxazine (A1).

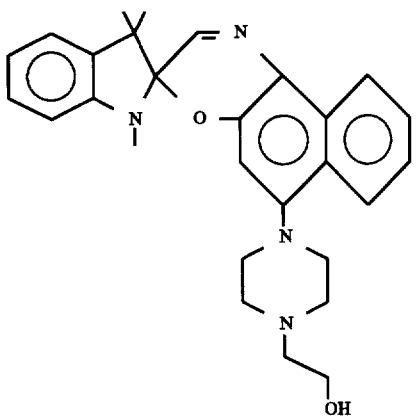

(A1)

20 g (153.8 moles) of N-2-hydroxyethyl piperazine and 5 g (28.9m moles) of 1,3,3,-trimethyl-2-methylene indoline are added, under a nitrogen flow, to a suspension of α-nitrose β-naphthol (10 g, 57.8 mmoles) in toluene (150 ml).

The resulting mixture is heated for 4 hours and 30 minutes before removing the solvent with a rotating evaporator.

120 ml of methanol are added to the residue and, after heating to reflux temperature, the resulting mixture is kept for 12 hours at room temperature.

The solid which has formed is filtered away and the limpid solution is dried at reduced pressure.

The residue obtained is dissolved in 120 ml of methylene chloride and the resulting solution is washed with 350 ml of water.

The solvent is removed from the organic phase, anhydrified on sodium sulphate, by means of the rotating evaporator.

The residue is dissolved under heat in 90 ml of methanol and the resulting solution is kept for 2 hours at room temperature.

A precipitate is formed which is filtered on buchener and washed with fresh methanol.

3.5 g of a greyish-white product are obtained which is used without further purification.

It was characterized as follows:

m.p. (measured in Differential Scanning Calorimetry or DSC): 168.9° C.

Mass spectrometry (m/e): ion [MH]$^+$: 456

$^1$H-NMR (200 MHz, CDCl$_3$-TMS ) δ (ppm): 1.33 ( 6H, s, 2 CH$_3$ in 3); 2.5–2.9 (10H, m, NCH$_3$, OH and 6H aliphatic); 3.0–3.15 (4H, m, H aliphatic); 3.65 (2H, t, —CH$_2$OH); 6.55 (1H, d, H in 7); 6.58 (1H, s, H in 5'); 6.87 (1H, t, H in 5); 7.07 (1H, d, H in 4); 7.19 (1H, t, H in 6); 7.34 (1H, t, H in 8'); 7.53 (1H, t, H in 9'); 7.61 (1H, s, CH on N); 8.0 (1H, d, H in 7'); 8.52 (1H, d, H in 10').

EXAMPLE 2

Preparation of 1,3-dihydro-6'-N[2(octadecanoyloxy)ethyl] piperazino-1,3,3-trimethyl spiro [2H indole-2,3'-[3H]-naphth-(2,1b)-(1,4) oxazine] (Ia).

1 ml of triethylamine and 0.81 ml (0.73 g=2.4 mmoles) of stearoyl chloride are added to a solution of 1,3-dihydro-6'-N(-2-hydroxyethyl) piperazino-1,3,3-trimethyl spiro [2H indole-2,3'-[3H]-naphth- (2,1b)-(1,4) oxazine](A1) (1g, 2,2 mmoles) in toluene (20 ml).

3 ml of triethylamine and 1.4 ml of acyl chloride are added to the reaction mixture over a period of 8 hours.

After an hour at room temperature, the resulting mixture is treated with 60 ml of 3.5% NaOH.

An emulsion is formed which is extracted 4 times with 100 ml of methylene chloride.

The reddish-purple coloured organic extracts are put together and anhydrified on sodium sulphate.

After the anhydrifying agent has been eliminated by filtration, 5 g of silica are added to the limpid solution.

The solvent is removed from the resulting suspension by the rotating evaporator, and a blue powder is obtained which is charged into a glass column containing 3 g of clean silica.

The silica column is eluated with 120 ml of ethyl acetate, and a reddish-purple solution is obtained from which the solvent is removed by means of the rotating evaporator.

Upon recrystallization of the residue with hexane (15 ml), 1.1g of a white product is obtained.

It has been characterized as follows:

Mass spectrometry (m/e): ion [ME]$^+$: 722.

$^1$H-NMR (200 MHz, CDCl$_3$-TMS) δ (ppm): 0.85 (3H, t, CH$_3$ of the aliphatic chain); 1.14–1.4 (34H, m, aliphatic chain plus 2 methyl groups in 3 ); 1.5–1.7 (2H, m, —CH$_2$—CH$_2$—COO—); 2.3 (2H, t, —CH$_2$—COO—); 2.67–2.86 (9H, m, NCH$_3$ and 6H aliphatic); 3.0–3.2 (4H, m, —(CH$_2$)$_2$N); 4.24 (2H, t, CH$_2$OCO); 6.55 (1H, d, H in 7); 6.57 (1H, s, H in 5'); 6.87 (1H, t, H in 5); 7.07 (1H, d, H in 4); 7.19 (1H, t, H in 6); 7.34 (1H, t, H in 8'); 7.52 (1H, t, H in 9'); 7.61 (1H, s, CH on N); 7.99 (1H, d, H in 7'); 8.52 (1H, d, H in 10').

EXAMPLE 3

Preparation of 1,3-dihydro-9'-dodecyloxy-1,3,3-trimethyl spiro [2H indole-2,3'-[3H]-naphth-(2,1b)-(1,4) oxazine] (Ib).

2 ml of triethylamine, 1 ml (4.16 mmoles) of 1-bromo dodecane and 0.2 g of Na$_2$CO$_3$ are added in this order to a suspension of 1,3-dihydro-9'-hydroxy-1,3,3-trimethyl spiro indole-2,3'-[3H]-naphth-(2,1b)-(1,4) oxazine] (prepared according to JP 90/41,388) (350 mg, 1 mmole) in toluene (5 ml).

The resulting mixture is heated to reflux temperature for 8 hours and, after one night at room temperature, 10 ml of water and 10 ml of toluene are added.

When the phases have been separated, the organic phase is washed with a further 10 ml of water and then anhydrified on sodium sulphate.

On eliminating the solvent at reduced pressure, a residue is obtained which is crystallized with hexane (10 ml).

230 m$_9$ of a white product are obtained.

It was characterized as follows:

Mass spectrometry (m/e): ion [MH]$^+$: 512.

$^1$H-NMR (200 MHz, CDCl$_3$-TMS) δ (ppm): 0.86 (3H, t, CH$_3$ of the aliphatic chain); 1–2 (26H, m, H aliphatic); 2.73 (3H, s, NCH$_3$); 4.15 (2H, t, —CH$_2$O); 6.55 (1H, d, H in 7); 6.81 (1H, d, H in 5'); 6.87 (1H, t, H in 5); 7.01 (1H, dd with J metha, H in 8'); 7.06 (1H, d, H in 4); 7.19 (1H, dt with J metha, H in 6); 7.54 (1H, d, H in 6'); 7.59 (1H, d, H in 7'); 7.69 (1H, s, CH on N); 7.81 (1H, d with J metha, H in 10').

EXAMPLE 4

Preparation of 1,3-dihydro-9'(isobutyloxyacetate)-1,3,3-trimethyl spiro [2H indole-2,3'-[3H]-naphth-(2,1b)-(1,4) oxazine] (B1).

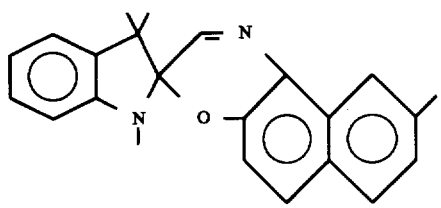
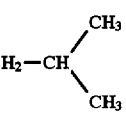

3 g (55 mmoles) of sodium methylate are added to a suspension of 1,3-dihydro-9'-hydroxy-1,3,3-trimethyl spiro [2H indole-2,3'-[3H]-naphth-(2,1b)-(1,4) oxazine] (prepared according to JP 90/41,388) (17 g, 50 mmoles) in isobutylic alcohol (60 ml), kept under a nitrogen flow at 80° C. 9.2 g (55 mmoles) of ethyl bromo acetate are added to the dark solution obtained.

The mixture is then heated to 80° C. for 1 hour before adding 30 ml of toluene necessary for dissolving the precipitate which has formed.

After a further hour at 80° C., the reaction mixture is cooled to room temperature before adding 50 ml of water and 3 g of active carbon.

The resulting suspension is filtered and the organic phase is separated from the aqueous solution.

The solvent is removed from the organic solution obtained with the rotating evaporator and the residue crystallized by adding 50 ml of ethyl alcohol.

16 g of a yellow product are thus obtained.

It was characterized as follows:

Mass spectrometry (m/e): ion [MH]$^+$: 458.

$^1$H-NMR (200 MHz, CDCl$_3$-TMS) δ (ppm): 0.92 (6H, d, the CH$_3$ of the isobutyl group); 1.32 (3H,s a CH$_3$ in 3); 1.33 (3H, s, a CH$_3$ in 3); 2.0 (1H, m, CH of the isobutyl group); 2.73 (3H, s, NCH$_3$); 4.03 (2H, d, —CH$_2$— of the isobutyl group); 4.83 (2H, s, —O—CH$_2$—COO—); 6.55 (1H, d, H in 7); 6.83 (1H, d, H in 5'); 6.87 (1H, t, H in 5); 7.04–7.23 (3H, m, H in 4, H in 6 and H in 8'); 7.55 (1H, d, H in 6'); 7.64 (1H, d, H in 7'); 7.67 (1H, s, CH on N); 7.8 (1H, d with J metha, H in 10').

EXAMPLE 5

Preparation of 1,3-dihydro-9'-(octadecyloxyacetate)-1,3,3-trimethyl spiro [2H indole-2,3'-[3H] naphth-(2,1b)-(1,4) oxazine] (Ic).

0.33 g (1.2 mmoles) of stearylic alcohol and 25 mg of tin dibutyl dilaurate are added to a solution of 1,3-dihydro-9'-(isobutyloxyacetate)-1,3,3-trimethyl spiro [2H indole-2,3'-[3H] naphth-(2,1b)-(1,4) oxazine] (B1) (0.5 g, 1.1 mmoles) in toluene (10 ml).

The resulting solution is heated to reflux temperature for 15 hours continuously distilling the solvent and replacing it with fresh toluene.

The solvent is then removed from the resulting mixture in the rotating evaporator and the residue is recrystallized with isopropylic alcohol.

The solid is filtered on büchener and then washed with isopropanol and methanol.

0.6 g of a white solid are thus obtained.

It was characterized as follows:

m.p. (measured in Differential Scanning Calorimetry or DSC): 72.7° C.

Mass spectrometry (m/e): ion [MH]$^+$: 654.

$^1$H-NMR (200 MHz, CDCl$_3$-TMS) δ (ppm): 0.85 (3H, t, CH$_3$ of the aliphatic chain); 1.1–1.4 (36H, m, 6H of the two methyls in 3 and 30H of the —CH$_2$— of the aliphatic chain); 1.68 (2H, t, —CH$_2$—CH$_2$—O—); 2.73 (3H, s, NCH$_3$); 4.22 (2H, t, —CH$_2$OCO); 4.81 (2H, s, —O—CH$_2$—COO); 6.55 (1H, d, H in 7); 6.84 (1H, d, H in 5'); 6.87 (1H, t, H in 5); 7.07 (1H, d, H in 4); 7.13 (1H, dd with J metha, H in 8'); 7.55 (1H, d, H in 6'); 7.64 (1H, d, H in 7'); 7.68 (1H, s, CH on N); 7.8 (1H, d, with J metha, H in 10').

EXAMPLE 6

Four mixtures are prepared (n. 1–4 in Table 1) composed of low density polyethylene in granules (Riblene CF 2200U - Enichem), of the stabilizer UV Chimasorb 944U (Ciba Geigy) and, in cases 2, 3 and 4 respectively, of photochromatic compounds A1, Ia and the compound 1,3-dihydro-6'-piperidino-1,3,3-trimethyl spiro [2H indole-2,3'-[3H]-naphth-(2,1b)-(1,4) oxazine] in the weight ratios specified in Table 1.

TABLE 1

| Mixture number | UV stabilizer (% w/w) | Photochromatic compound (% w/w) |
|---|---|---|
| 1 | 0.2 | — |
| 2 | 0.2 | 0.11 |
| 3 | 0.2 | 0.175 |
| 4 | 0.2 | 0.1 |

The photochromatic compounds were used in different weight quantities to obtain equal molar concentrations.

The mixtures obtained were transformed into films with a thickness of 150 μm by means of extrusion.

The extrusions were carried out in a Plasticorder Brabender equipped with a 19 mm diameter barrel.

The temperature profile along the extruder was: 170° C.–180° C.–190° C.–200° C.–210° C.

The photochromatic films obtained were evaluated by visual inspection, immediately after preparation and then replaced in darkness.

The evaluations were repeated after 7 and after 60 days. The results are shown in Table 2.

TABLE 2

| Mixture number | Evaluation immediately after film preparation | Evaluation after seven days | Evaluation after sixty days |
|---|---|---|---|
| 1 | Transparent, homogeneous film | Transparent, homogeneous film | Transparent, homogeneous film |
| 2 | Transparent, homogeneous film | Transparent, homogeneous film | Very evident blooming |
| 3 | Transparent, homogeneous film | Transparent, homogeneous film | Transparent, homogeneous film |
| 4 | Transparent, homogeneous film | Traces of blooming | Very evident blooming |

Blooming has a negative effect on the photochromatic activity of the product, as can be seen in Table 3 which shows the optical density values (D.O.) of the film at 358 nanometers (nm) ($l_{max}$ of the colourless form) and the transmittance percentage variation at 25° C. (DT ) between 400 and 700 nanometers associated with the activation process.

TABLE 3

| Mixture number | D.O. (358 nm) | DT (25° C.) |
| --- | --- | --- |
| 2 | 0.458 | 0.57 |
| 3 | 0.573 | 18.52 |
| 4 | 0.468 | 6.79 |

We claim:

1. Photochromatic and thermochromatic compounds, belonging to the group of spiro-indoline-oxazines, which are defined by the following general formula (I):

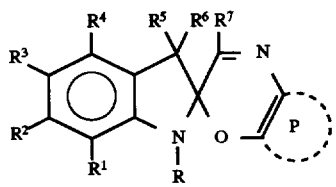

where R represents a linear or branched $C_1$–$C_5$ alkyl group or a $C_1$–$C_5$ alkyl group substituted with frown 1 to 5 halogen atoms selected from the group consisting of fluorine, chlorine, bromine and iodine atoms, hydroxy groups, $C_1$–$C_5$ alkoxy groups, $C_1$–$C_5$ alkyl carboxy groups, or cyano groups; a $C_2$–$C_5$ alkenyl group; a phenyl group; or a benzyl group;

where $R^1$ to $R^4$, which may be the same or different, each independently represent a hydrogen atom; a linear or branched $C_1$–$C_5$ alkyl group; a $C_1$–$C_5$ alkyl group substituted with 1 to 5 halogen atoms selected from the group consisting of fluorine, chlorine, bromine and iodine atoms, hydroxy groups, $C_1$–$C_5$ alkoxy groups, $C_1$–$C_5$ alkyl carboxy groups, or cyano groups; a $C_2$–$C_5$ alkenyl group; a benzyl group; a halogen atom selected from the group consisting of fluorine, chlorine, bromine and iodine; a hydroxy group; a $C_1$–$C_5$ alkoxy group; an amino group; a mono-alkyl ($C_1$–$C_5$) amino group, a di-alkyl ($C_1$–$C_5$ ) amino group or a cyclo-alkyl ($C_3$–$C_{10}$) amino group; a piperidine, piperazine or morpholino group; a carboxyl group; a $C_1$–$C_5$ alkyl carboxy group or a $C_2$–$C_5$ alkenyl carboxy group; an amidic carboxy group; a substituted N-alkyl ($C_1$–$C_5$) amidic carboxy group or a substituted N,N-dialkyl ($C_1$–$C_5$) amidic carboxy group; a cyano group; a nitro group; a sulphonic group; a sulphonic alkyl ($C_1$–$C_5$) group; a trifluoromethane-sulphonic group; a sulphonic aryl group selected from the group consisting of benzene sulphonic, p-toluene sulphonic, and p-chlorotoluene sulphonic groups; an aryl group selected from the group consisting of phenyl, biphenyl, and naphthyl groups; or an acyclic group selected from the group consisting of an alkyl ketone and an aryl ketone;

where two consecutive substituents from $R^1$ to $R^4$ represent fusion points with other aromatic, heterocyclic or quinonic rings;

where $R^5$ and $R^6$, which may be the same or different, each independently represent a linear or branched $C_1$–$C_5$ alkyl group; a phenyl group; or $R^5$ and $R^6$, together with the carbon atoms to which they are linked, jointly represent a $C_4$–$C_7$ cycloalkyl group;

where $R^7$ represents a hydrogen atom; a linear or branched $C_1$–$C_5$ alkyl group; a phenyl group; a halogen atom selected from the group consisting of fluorine, chlorine and bromine; a $C_1$–$C_5$ alkoxy group; or a phenoxy group;

P represents a monocyclic or polycyclic arenic nucleus selected from formulae (II), (III), (IV), (V) and (VI):

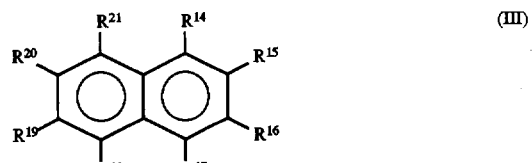

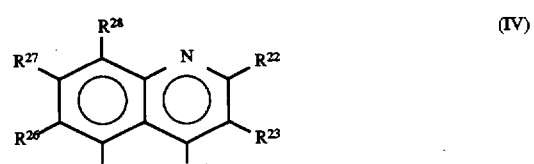

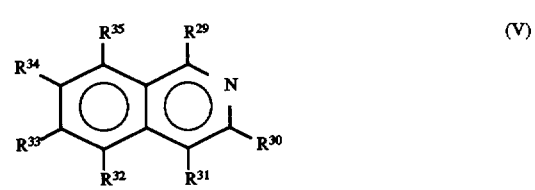

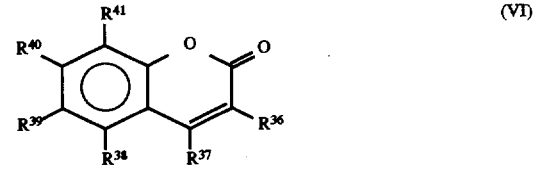

wherein $R^8$ to $R^{41}$, which may be the same or different, each independently represent a hydrogen atom; a linear or branched $C_1$–$C_5$ alkyl group; a $C_1$–$C_5$ alkyl group substituted with 1 to 5 halogen atoms selected from the group consisting of fluorine, chlorine, bromine and iodine atoms, hydroxy groups, $C_1$–$C_5$-alkoxy groups, $C_1$–C5 alkyl carboxy groups, or cyano groups; a $C_2$–$C_5$ alkenyl group; a benzyl group; a halogen atom selected from the group consisting of fluorine, chlorine, bromine and iodine; a hydroxy group; a $C_1$–$C_5$ alkoxy group; an amino group; a mono-alkyl ($C_1$–$C_5$ ) amino group, a di-alkyl ($C_2$–$C_5$) amino group or a cyclo-alkyl ($C_3$–$C_{10}$) amino group; a piperidine, piperazine or morpholino group; a carboxyl group; a $C_1$–$C_5$ alkyl carboxy group or a $C_2$–$C_5$ alkenyl carboxy group; an amidic carboxy group; a substituted N-alkyl ($C_1$–$C_5$) amidic carboxy group or a substituted N,N-dialkyl ($C_1$–$C_5$ ) amidic carboxy group; a cyano group; a nitro group; a sulphonic group; a sulphonic alkyl ($C_1$–$C_5$) group; a trifluoromethane-sulphonic group; a sulphonic aryl group selected from the group consisting of benzene sulphonic, p-toluene sulphonic, and p-chlorotoluene sulphonic groups; an aryl group selected from the group consisting of phenyl, biphenyl, and naphthyl groups; or an acyclic group selected from the group consisting of an alkyl ketone and an aryl ketone;

where at least two contiguous substituents from $R^8$ to $R^{13}$, $R^{14}$ to $R^{21}$, $R^{22}$ to $R^{28}$, $R^{30}$ to $R^{35}$, or $R^{36}$ to $R^{41}$ represent fusion sites with the oxazinic ring; and where at least one of the substituents selected from R to $R^{41}$ represents a $R^{42}$ group, a —$COOR^{42}$ group, a —$CONHR^{42}$ group, a —$CONR^{42}R^{43}$ group, a —$COR^{42}$ group, a OH—CH—$R^{42}$ group, a OH—C—$R^{42}R^{43}$ group, a —$OR^{42}$ group, a —$NHR^{42}$ group, a —$NR^{42}R^{43}$ group, a —$SR^{42}$ group, a —O—$(CH_2)_n$—$COOR^{42}$ group, a —O—$(CH_2)_n CONHR^{42}$ group, or a —O—$(CH_2)_n$—$CONR^{42}R^{43}$ group, where $R^{42}$ and $R^{43}$ are independently a linear or branched $C_9$–$C_{30}$ alkyl group, a $C_9$–$C_{30}$ alkyl group substituted with 1–30 halogen atoms selected from the group consisting of fluorine, chlorine, bromine and iodine, or a $C_9$–$C_{30}$ alkenyl group and where n varies from 0 to 10.

2. Photochromatic and thermochromatic compounds belonging to the group of spiro-indoline-oxazines, according to claim 1, wherein, when R is the alkyl group, R is a methyl or an ethyl group; wherein, when R is the alkenyl group, R is a 2-allyl group; wherein, when R is the $C_1$–$C_5$ alkyl group substituted with hydroxy groups, R is a 2-hydroxyethyl group; wherein, when R is the $C_1$–$C_5$ alkyl group substituted with the $C_1$–$C_5$ alkoxy groups, R is a 2-methoxyethyl group; or wherein, when R is the $C_1$–$C_5$ alkyl group substituted with the $C_1$–$C_5$ alkyl carboxy groups, R is a 2-carboxymethyl ethyl group;

wherein, when $R^1$ to $R^4$ are the halogen atoms, $R^1$ to $R^4$ are the fluorine, chlorine or bromine atoms; wherein, when $R^1$ to $R^4$ is the $C_1$–$C_5$ alkyl group, $R^1$ to $R^4$ are a methyl group or an isopropyl group; wherein, when $R^1$ to $R^4$ are the $C_1$–$C_5$ alkoxy groups, $R^1$ to $R^4$ is a methoxy group; wherein, when $R^1$ to $R^4$ are the $C_1$–$C_5$ alkyl carboxy groups, $R^1$ to $R^4$ are carboxymethyl group or; wherein, when $R^1$ to $R^4$ are substituted N, N-dialkyl ($C_1$–$C_5$) amdic carboxy group, $R^1$ to $R^4$ are N,N-dimethylcarboxyamide group;

wherein, when $R^5$ and $R^6$ are the $C_1$–$C_5$ alkyl groups, $R^5$, $R^6$, or both $R^5$ and $R^6$ are methyl groups; or wherein, when $R^5$ and $R^6$ are the cycloalkyl groups, $R^5$, $R^6$, or both $R^5$ and $R^6$ are cyclohexyl groups;

wherein, when $R^7$ is the halogen atom, $R^7$ is a chlorine atom; wherein, when $R^7$ is the $C_1$–$C_5$ alkyl group, $R^7$ is a methyl group; or wherein, when $R^7$ is the $C_1$–$C_5$ alkoxy group, $R^7$ is a methoxy group.

3. Photochromatic and thermochromatic compound which is 1,3-dihydro-9-dodecyloxy-1,3,3-trimethyl spiro 2H indole-2,3'-[3]-naptho-(2,1b)-(1,4) oxazine having the formula

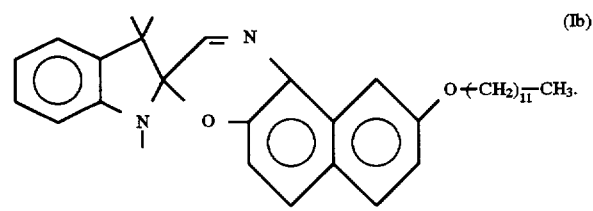

4. Photochromatic polymeric composition composed of at least one compound according to claim 1 and at least one polymer selected from the group consisting of high density polyethylene, low density polyethylene, ethylene-vinyl acetate copolymer, polyether amide, polymethyl methacrylate, polyvinyl alcohol, polyvinyl butyryl, cellulose acetate butyrate, epoxy, polysiloxane, polyurethane, polycarbonate, polydiethylene glycol, and bis(allyl carbonate).

5. Photochromatic polymeric composition according to claim 4, wherein the polymer is the low density polyethylene.

6. Photochromatic and thermochromatic compound 1,3-dihydro-6'-N[2-octadecanoyloxy)-ethyl]piperazino-1,3,3-trimethyl spiro [2H indole-2,3'- [3H]-naphth-(2,1b)-(1,4) oxazine having the formula:

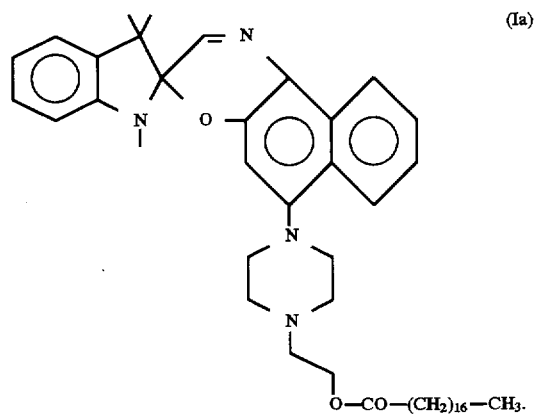

7. Photochromatic and thermochromatic compound which is 1,3 dihydro-9'-(octadecyloxyacetate)-1,3,3-trimethyl spiro[2H indole-2,3'-[3H]-naphtho-(2,1b)-(1,4 oxazine) having the formula:

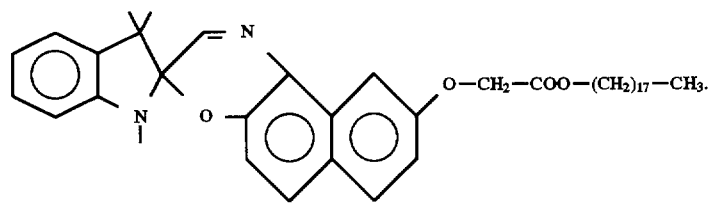

8. Photochromatic and thermochromatic compounds, belonging to the group of spiro-indoline-oxazines, which are defined by the following general formula (I):

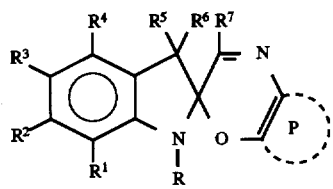
(I)

where R represents a linear or branched $C_1$–$C_5$ alkyl group a $C_1$–$C_5$ alkyl group substituted with from 1 to 5 halogen atoms selected from the group consisting of fluorine, chlorine, bromine and iodine atoms, hydroxy groups, $C_1$–$C_5$ alkoxy groups, $C_1$–$C_5$ alkyl carboxy groups, or cyano groups; a $C_2$–s alkenyl group; a phenyl group; or a benzyl group;

wherein the substituents $R^1$ to $R^{41}$ are selected from the formulae (VII), (VIII), (IX), (X), (XI), (XII), and (XIII):

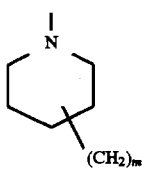
(VII)

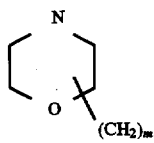
(VIII)

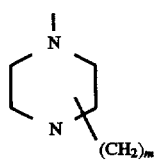
(IX)

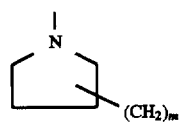
(X)

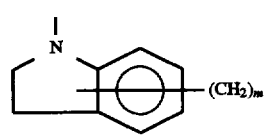
(XI)

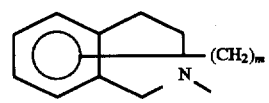
(XII)

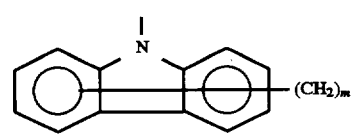
(XIII)

where m is an integer from 0 to 10, and wherein P represent as a monocyclic or polycyclic arenic nucleus of the benzene, naphthalene, quinoline, isoquinoline or cumarine type which can be respectively represented with the formulae (II), (III), (IV), (V) and (VI):

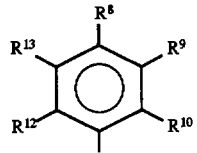
(II)

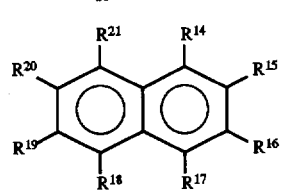
(III)

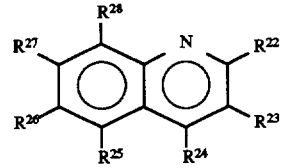
(IV)

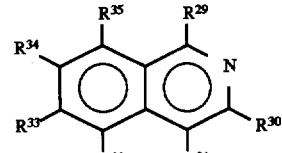
(V)

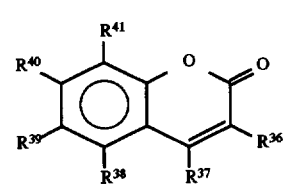
(VI)

where at least two continuous substituents from $R^8$ to $R^{13}$ in formula (II), $R^{14}$ to $R^{21}$ in formula (III), $R^{22}$ to $R^{28}$ ill formula (IV), $R^{30}$ to $R^{35}$ in formula (V), and $R^{36}$ to $R^{41}$ in formula (VI) represent the fusion sites with the oxazinic ring.

9. The photochromatic and thermochromatic compounds of claim 1, wherein, when $R^1$ to $R^4$ is the aryl ketone, $R^1$ to $R^4$ is benzyl ketone.

10. The photochromatic and thermochromatic compounds of claim 1, wherein, when $R^8$ to $R^{41}$ is the aryl ketone, $R^8$ to $R^{41}$ is benzyl ketone.

* * * * *

UNITED STATES PATENT AND TRADEMARK OFFICE
CERTIFICATE OF CORRECTION

PATENT NO. : 5,730,908

DATED : March 24, 1998

INVENTOR(S) : Nereo Nodari, Pietro Allegrini and Luciana Crisci

It is certified that error appears in the above-identified patent and that said Letters Patent is hereby corrected as shown below:

On the title page, please change the Filing Date of the parent U.S. Application No. 08/217,075 from "September 21, 1992" to -- July 21, 1992 --.

Signed and Sealed this

Twenty-ninth Day of September, 1998

Attest:

BRUCE LEHMAN

Attesting Officer

Commissioner of Patents and Trademarks